US008835109B2

(12) United States Patent
Burns

(10) Patent No.: US 8,835,109 B2
(45) Date of Patent: Sep. 16, 2014

(54) METHOD FOR DETECTION AND/OR ANALYSIS OF YEAST AND MOLD IN FILTERABLE LIQUIDS

(75) Inventor: Frank R. Burns, Philadelphia, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 598 days.

(21) Appl. No.: 12/742,516

(22) PCT Filed: Nov. 12, 2008

(86) PCT No.: PCT/US2008/083204
§ 371 (c)(1),
(2), (4) Date: Jun. 9, 2010

(87) PCT Pub. No.: WO2009/064766
PCT Pub. Date: May 22, 2009

(65) Prior Publication Data
US 2011/0104672 A1    May 5, 2011

Related U.S. Application Data

(60) Provisional application No. 61/003,345, filed on Nov. 16, 2007.

(51) Int. Cl.
*C12Q 1/68* (2006.01)
(52) U.S. Cl.
CPC .................. *C12Q 1/6895* (2013.01)
USPC ........................................................ 435/6.1
(58) Field of Classification Search
USPC ........................................................ 435/6.1
See application file for complete search history.

(56) References Cited

U.S. PATENT DOCUMENTS 7,291,465 B2 * 11/2007 Karaolis ....................... 435/6.13
7,776,530 B2 * 8/2010 Ollikka et al. ................ 435/6.11

FOREIGN PATENT DOCUMENTS

WO    WO98/11257 A1    3/1998
WO    WO03/008636 A2    1/2003

OTHER PUBLICATIONS

Brinkman et al. (Appl Environ Microbiol. Mar. 2003;69(3):1775-82).*
Robins et al. (Biochem.J. (1981) 194, 63-70).*
Schumann et al. (International Biodeterioration and Biodegradation. vol. 55, No. 3, Apr. 2005).*
Zhou et al. (Mol Cell Probes. Dec. 2000;14(6):339-48).*
Brinkman, N. et al.; "Evaluation of a Rapid, Quantitative Real-Time . . . ", Applied and Environmental Microbiology, vol. 69, No. 3, Mar. 2003, p. 1775-1782, XP002511491.
Schumann, Rena, et al.; "Chlorophyll extraction methods for the quantification . . . ", International Biodeterioration & Biodegradation 55 (2005) p. 213-222.
Eikrem, Wneche, et al.; "*Florenciella parvula* gen. et sp. nov. (Dictyochophyceae, Heterokontophyta) a small flagellate . . . " Phycologia, vol. 43 (6), Dec. 2004 p. 658-668.
Rossi, S., et al.; "Lipid biomarkers and trophic linkages between phytoplankton, zooplankton and . . . "; Journal of Plankton Research, vol. 28, No. 6, Jun. 2006 p. 551-556.
Borman, Andrew, et al.; "Ultra-rapid preparation of total genomic DNA from isolates of yeast and mould using Whatman FTA . . . "; Medical Mycology, Aug. 2006, 44, p. 389-398.

* cited by examiner

*Primary Examiner* — Cynthia B Wilder

(57) ABSTRACT

This invention is a process for preparing a food or beverage sample containing yeast or mold cells for analytical testing. The food sample is prepared into the form of a filterable liquid, and then filtered using a glass microfiber filter. The filter containing the fungal cell retentate is then placed into a disruption vessel and bead beaten until the glass microfiber filter is completely disrupted into glass fibers in suspension. An aliquot can then be tested directly using melting curve analysis of PCR amplification product derived from the nucleic acids of the sample to detect the presence of the fungal cells from the sample.

11 Claims, No Drawings

METHOD FOR DETECTION AND/OR ANALYSIS OF YEAST AND MOLD IN FILTERABLE LIQUIDS

CROSS-REFERENCE TO RELATED APPLICATION

This application claims priority from U.S. Provisional Application Ser. No. 61/003,345, filed Nov. 16, 2007, which is incorporated by reference herein in its entirety.

FIELD OF THE INVENTION

This invention relates to analytical testing of samples in the field of microbiology and molecular biology. In particular, it relates to preparation of yeast and fungal cell samples that are in a filterable-liquid form for subsequent analysis of the intracellular nucleic acid components of the samples.

BACKGROUND

Analysis and detection of pathogens in food and other types of samples involves multiple aspects. One aspect often involves growing and enriching a food sample to increase the number of target micro-organisms in the sample up to detectable (or more readily detectable) levels. For example, U.S. Pat. No. 6,312,930; WO 98120148; U.S. Pat. No. 5,843,669; U.S. Pat. No. 5,145,786; and EP 1 253 203 published Oct. 30, 2002, discuss enrichment and pre-enrichment of such samples.

Another aspect of analysis and detection of pathogens in food and other types of samples relates to isolation or collection of the cells in the sample so that such cells can be conveniently further processed, which processing may include disruption of the cells if the analysis relates to intracellular components of the cells. For example, if the sample aliquot contains yeast, fungal cells or spores, and it is desired to analyze the nucleic acid contained within the cells or spores, the cells or spores are optionally enriched, and then must be collected and disrupted to release their intracellular contents, including the nucleic acids. The process of collecting fungal cells prior to analysis often involves filtration, using for example vacuum filtration. The collected filtration retentate, which comprises the cells and spores of the fungal cells, must then traditionally be removed from the surface of the filtration medium, which typically comprises a filter paper, prior to cellular disruption.

One method of cell disruption involves subjecting cells or spores to forces which mechanically disrupt the cell walls, cell membrane, and other component structures of the cells or the spores, to release the internal cell contents into solution. For example, in a technique referred to in the art as "bead beating," as described in references WO 98/11257 and WO 2003008636, a sample solution comprising cells or spores is introduced into a container having physically disrupting elements. The sample solution is agitated to cause disruptive contact between the cells or spores and the disrupting elements, sufficient to disrupt the cells or spores and release their contents. Such mechanical disruption can optionally be followed by chemical or enzymatic lysis to complete the disruption or further digest the remaining cellular debris.

In a typical prior art method, a sample solution, which optionally has been previously enriched and filtered, can be introduced into a test tube containing disruption beads. The combined solution containing the target micro-organisms and the beads is then subjected to an application of force (for example, centrifuge, vortex, etc.), which physically disrupts the cells. The solution containing the disrupted cellular content, for example the released nucleic acids, is then suitable for analysis, including PCR-based detection analysis.

In some prior art methods involving algae, disruption of filtered cells is carried out without first removing the filter retentate from the filtration medium, i.e. disrupting the entire filter and the accompanying retentate. For example, methods involving cell disruption of algae on a filtration medium without first removing the retentate from the filtration medium are described in Schumann et al., *Chlorophyll extraction methods for the quantification of green microalgae colonizing building facades, International Biodeterioration & Biodegradation*, vol. 55, pp. 213-22 (2005); Rossi et al., *Lipid biomarkers and trophic linkages between phytoplankton, zooplankton and anchovy (Engraulis encasicolus) larvae in the NW Mediterranean, Journal of Plankton Research*, vol. 28, pp. 551-62 (2006); and Eikrem et al., *Florenciella parvula gen. et ap. Nov. (Dictyochophycae, Heterokontophyta), a small flagellate isolated from the English Channel, Phycologia*, vol. 43, pp. 658-68 (2004). In these prior art methods, the algae are filtered onto glass fiber filters (e.g., Whatman GF/F filters) and then the filters are placed into a physical disruption vessel (e.g., a Vibrogen IV bead mill) where the filter and accompanying cells are disrupted by bead beating. It should be noted that, in the cited references involving disruption of algae without prior removal of retentate from the filtration medium, the technique is employed specifically to release and characterize chlorophyll and pigments for further analysis, and not to release and examine nucleic acids.

An additional aspect of analysis and detection of pathogens in food and other types of samples relates to the actual method of detection utilized after the cells have been obtained. Frequently, detection methods are used which employ the polymerase chain reaction (PCR) method of nucleic acid amplification. One such detection method involves melting curve analysis of PCR amplification products, which method is described in detail in PCT Publication Nos. WO 97/11197 and WO 00/66777 and U.S. Pat. No. 6,312,930.

SUMMARY OF THE INVENTION

The present invention is useful for detection and analysis of fungal cells in various mediums, particularly in food or beverage samples, because it enables elimination of time-consuming steps in prior art methods of preparing such samples for analytical testing. Specifically, if filtration is used as a method to collect cells prior to mechanical disruption for analysis of subcellular components, by employing the present invention it will be unnecessary to remove the cellular retentate from the filtration medium prior to disruption of the cells and it will be unnecessary to clear the remaining microscopic particles of the filtration medium from the sample following disruption. The method of the present invention is applicable in analytical methods for qualitative detection, i.e., a presence or absence of a target fungal cell or a component of such cells, or for quantitative assessment, i.e., enumeration of the number of target cells or the amount present of a component of such cells. Depending upon the use and tolerance-limit specified, the present invention can be used without any enrichment of fungal samples, with short-term enrichment of samples, or with long-term enrichment of samples. And such enrichment may occur prior to filtration of the cells, or subsequent to filtration of the cells, or at both times. Further, such enrichment can be performed in any suitable vessel within the process used for analytical testing, for example, in the vessel used for disruption of the cells after the filter paper is placed in such vessel, or in the vessel holding the filterable liquid prior to filtration. In the present invention, the fungal enrichment step(s) will often include exposure of the sample to antibacterial agents such as bacteriostatics or bactericidal agents.

In one aspect, the present invention relates to a process for preparing a sample comprising fungal cells for analytical testing, the process comprising the steps of preparing said sample in the form of a filterable liquid, filtering the filterable liquid using a suitable filtration medium wherein said fungal cells form a retentate on said filtration medium, transferring said filtration medium to a vessel suitable for disrupting the filtration medium by mechanical means; simultaneously disrupting said cellular retentate and said filtration medium using mechanical means with a force sufficient to disrupt said filtration medium into microscopic particles; wherein the nucleic acids of the fungal cells of the cellular retenate are suitable for analytical testing without prior removal of the remaining microscopic particles of the filtration medium.

In a preferred embodiment, the present invention relates to a process for preparing a sample comprising fungal cells for analytical testing, comprising the steps of preparing said sample in the form of a filterable liquid, filtering the filterable liquid by vacuum filtration using a glass microfiber filter wherein said fungal cells form a retentate on said filter, transferring said filter to a vessel suitable for disrupting the filter by mechanical means comprising bead beating; simultaneously disrupting said cellular retentate and said filter by bead beating with a force sufficient to disrupt said filter into individual glass fibers in suspension; wherein the nucleic acids of the cellular retenate are suitable for PCR and melting curve analysis without removal of the glass fibers of the filter.

In all embodiments of the process of the invention, it should be understood that the step of preparing a sample in the form of a filterable liquid is only necessary if, and to the extent, the initial sample to be tested is not already in such form.

DESCRIPTION OF PREFERRED EMBODIMENTS

Although methods and materials similar or equivalent to those described herein can be used in the practice or testing of the present invention, suitable methods and materials are described herein. However, the materials, methods, and examples herein are illustrative only and, except as specifically stated, are not intended to be limiting.

DEFINITIONS

Unless otherwise defined, all technical and scientific terms used herein have the same meaning as commonly understood by one of ordinary skill in the art to which this invention belongs. In case of conflict, the present specification, including definitions, will control.

Unless stated otherwise, all percentages, parts, ratios, etc., are by weight.

When an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

When the term "about" is used in describing a value or an end-point of a range, the disclosure should be understood to include the specific value or end-point referred to.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive 'or' and not to an exclusive 'or.' For example, a condition A or B is satisfied by any one of the following: A is true (or present) and B is false (or not present), A is false (or not present) and B is true (or present), and both A and B are true (or present).

Use of "a" or "an" are employed to describe elements and components of the invention. This is done merely for convenience and to give a general sense of the invention. This description should be read to include one or at least one, and the singular also includes the plural unless it is obvious that it is meant otherwise.

Each document cited herein is incorporated by reference in its entirety.

The term "filterable liquid" will be well understood by those skilled in the art to be functionally dependent upon the system selected for filtration of a particular liquid sample, and as such, a "filterable liquid" may include any liquid or partially liquid form in which at least some components are able to pass through the particular filtration medium at the conditions selected. For example, the viscosity and particulate levels of the starting liquid are factors determining whether a liquid is a "filterable liquid" for the desired system. Other important factors include the type of filtration medium selected. If a filter paper medium is selected, the structural integrity and strength of such filter, the porosity of such filter, and the pore sizes of such filter will be important in determining whether a liquid sample is a "filterable liquid" for such system. The temperature of the "filterable liquid" may influence whether such liquid is "filterable", and also the pressure which is applied to system across the filter will effect whether a liquid sample is a "filterable liquid" in the system desired.

The term "fungal cell" includes all organisms commonly known within these classifications, particularly including yeasts and molds.

The term "sample comprising fungal cells" is intended to be nonlimiting and includes portions, pieces or aliquots of any medium or composition in which fungal cells may be present. The initial sample may be in a liquid, semi-liquid or solid form, and may, by way of example only, comprise environmental samples, such as river water or soil; pieces of deteriorating housing materials, such a wall board or furnace filters; industrial samples, such as sludge from pipe linings or industrial waste; or, preferably, food or beverage samples, such as juices, meats, spices, or soft drinks. The terms "food" and "beverage" include all items suitable for human or animal consumption, including liquid, solid, semi-solid, and suspension products.

The term "subcellular components" refers to components within fungal cells such as, for example, proteins or nucleic acids. Subcellular components also include portions of the cell walls and outer membranes of yeast and mold cells that become accessible for testing when the cells are disrupted.

The terms "nucleic acid", polynucleotide", "polynucleotide sequence", "nucleic acid sequence", and "nucleic acid fragment" encompass all varieties of nucleotide sequences. This encompasses a polymer of RNA or DNA that is single- or double-stranded, that optionally contains synthetic, non-natural or altered nucleotide bases. If in the form of a polymer of DNA, these may be comprised of one or more strands of cDNA, genomic DNA, synthetic DNA, or mixtures thereof.

"Polymerase chain reaction" is abbreviated PCR.

The term "amplification product" refers to nucleic acid fragments produced during a primer-directed amplification reaction. Typical methods of primer-directed amplification include polymerase chain reaction (PCR), ligase chain reaction (LCR), or strand displacement amplification (SDA). If PCR methodology is selected, the replication composition may comprise the components for nucleic acid replication, for example: nucleotide triphosphates, two (or more) primers with appropriate sequences, thermostable polymerase, buffers, solutes and proteins. These reagents and details describing procedures for their use in amplifying nucleic acids are provided in U.S. Pat. No. 4,683,202 (1987, Mullis, et al.) and U.S. Pat. No. 4,683,195 (1986, Mullis, et al.). If LCR methodology is selected, then the nucleic acid replication compositions may comprise, for example: a thermostable ligase (e.g., *T. aquaticus* ligase), two sets of adjacent oligonucleotides (wherein one member of each set is complementary to each of the target strands), Tris-HCl buffer, KCl, EDTA, NAD, dithiothreitol and salmon sperm DNA. See, for example, Tabor et al., *Proc. Acad. Sci. U.S.A.*, 82:1074-1078 (1985)).

The term "primer" refers to an oligonucleotide (synthetic or occurring naturally), which is capable of acting as a point of initiation of nucleic acid synthesis or replication along a complementary strand when placed under conditions in which synthesis of a complementary strand is catalyzed by a polymerase.

The term "probe" refers to an oligonucleotide (synthetic or occurring naturally) that is complementary (though not necessarily fully complementary) to a polynucleotide of interest and forms a duplexed structure by hybridization with at least one strand of the polynucleotide of interest.

The term "analytical testing" includes any test that can be applied to cells to determine the presence of such cells, number of such cells, identity of such cells, or other aspects relating to characteristics of such cells. Analytical testing includes primer-directed amplification assay methods, such as thermal cycling methods (e.g., PCR, RT-PCR, and LCR), isothermal methods, and strand displacement amplification (SDA), as well as nucleic acid hybridization methods. Analytical testing further includes homogenous detection (e.g. melting curve analysis and 5' nuclease detection), standard non-denaturing gel electrophoresis (e.g., acrylamide or agarose) detection, denaturing gradient gel electrophoresis detection, and temperature gradient gel electrophoresis detection of primer-directed amplification products.

The process of the present invention comprises the following steps:

Sample Preparation

A product to be tested for the presence or absence of particular fungal cells must initially be either in the form of a filterable liquid, or must be converted into the form of a filterable liquid, so as to be in a form capable, subsequently, of filtration. For example, a product such as orange juice or a sugary beverage could be used "as is" or it could be diluted to a desired level by addition of water or other inert liquid so that it is amenable to filtration. However, solid or semi-solid items such as a paste that is a precursor to soups, or a cream used as a personal cosmetic, or a piece of processed meat, can also be made amenable to filtration by adding liquids such as water and then physically blending, mixing or 'liquefying' the sample using simple stirring, or strong force if necessary, to disperse and disrupt the initial sample into a homogeneous or partially homogeneous filterable liquid form. The term "liquid" is not used herein in a limiting manner in a strict chemical sense to refer only to solutions or homogeneous liquids. Applicants herein use the term liquid to include any fluid-form sample that may include, for example, a pure liquid, a heterogeneous dispersion, a solution, a colloidal suspension or other fluidized form.

Filtration

An aliquot of the filterable liquid sample, or even a large volume of the filterable liquid sample, is filtered through a suitable filtration medium. Depending upon requirements and desire, a sample may or may not be enriched prior to filtration. Suitable filtration media for use in the present invention include those that have a pore size capable of retaining fungal cells in the sample and are also able to be physically disrupted during the mechanical disruption step. This latter requirement makes it such that, in the present invention, the filter does not have to be separated from the cellular retentate prior to disruption of the fungal cells. Preferred filtration media for the present invention are glass microfiber filters having a pore size of 0.5-4.0 µm. For example, Whatman GF/A 25 mm glass microfiber filters with a 1.6 µm nominal pore size (catalog #1820-025) are used successfully in the process of the invention when routine bench top vacuum filtration is used to filter and bead beating is used to disrupt the cells.

By filtration is meant the separation of the component called the "retentate" from the rest of the filterable liquid based upon the size of the particles in the retentate. The retentate comprises particulates that were not able to pass through the pores in the filtration medium. The component of the sample passing through the filtration medium is called the "permeate" or the "filtrate." In the case of the present invention, the retentate comprises the fungal cells. Commonly employed methods of filtration include vacuum-filtration, pressure filtration, centrifugal filtration, vortex-filtration, gravity separation, etc. Filtration methods, including variables such as temperature of the filterable liquid and the pressure applied across the filtration medium, are well-known in the art and are considered to be within the scope of use in the present invention. Preferred filtration methods are vacuum filtration and centrifugal filtration.

After filtration, instead of removing and collecting the retentate residue that comprises target micro-organisms, in the present invention, the entire filtration medium with the accompanying retentate is transferred to a disruption vessel for disruption, thus providing time savings, as well as greater accuracy and reproducibility in the testing step. It will be appreciated that, in many current analytical formats, multiple samples are processed together. The invention thus finds particular applicability in large scale, repetitive testing processes, where the omission of the separate step of removal of retentate sample from the filtration medium has considerable practical value. Further, if the filtration is carried out in such a manner that the filter is already present in the disruption vessel during the filtration step, the need for any such transferring is avoided. Thus, transferring to a suitable vessel for disruption is herein defined as performing such transfer only when the filtration medium is not already so present in a suitable vessel for disruption.

Enrichment and Growth

Enrichment, which means placing at least a portion of the sample into a medium at conditions which optimize selective growth of the fungal cells to be tested, is an optional step. In some embodiments it may be necessary, depending upon how many yeast or mold cells are present in the initial sample to be tested, i.e. enrichment may be required if the initial concentration for the "target" micro-organism is below the detection level. Further, enrichment may be desired to generally increase the robustness of detection, because a higher concentration of the "target" micro-organisms, as a result of enrichment, will enhance the probability of detection when low numbers of target organisms are present in the initial sample.

Enrichment and/or growth, as used herein, will be understood as including enrichment, growth, pre-enrichment, selective enrichment, or any combination thereof. Enrichment and/or growth of a sample in enrichment medium are well known to those in the art. Further, protocols for enrichment and/or growth are known in the art and are also disclosed in publicly-available FDA protocols.

In accordance with the invention, in the embodiments wherein enrichment is desired or required, the enrichment step may precede the filtration step, may follow the filtration step, or may be performed both prior to and after the filtration step.

Disruption of the Cells or Spores and the Filtration Medium

Following filtration, the filtration medium along with the retentate is transferred to a disruption vessel or chamber. The disruption vessel will contain disrupting elements. The disrupting elements are physical elements capable of disrupting tissue, cells, spores and such other cells or cellular components to release their intracellular contents in the presence of an applied force.

The elements may comprise particulate glass, plastic, metal, sand, or other mineral-based materials. Preferred particulate materials are glass beads.

Particulate materials of different shapes can be used in the present invention. Nominally spherical particulate elements are preferred. Also preferred are particulate elements that have sharp edges, jagged edges, or sharp points that will aid in disruption process. Disrupting elements that have irregular shapes can also be used.

The size of the disrupting elements may vary, but in the case of glass beads, a mean diameter of about 0.5 mm is currently preferred. Generally, the disrupting elements are present in an effective amount to interact with the cells, tissue or spores to an extent that the intracellular contents of the sample and/or the fungal cells in the sample are released into the disruption vessel. For this system the preferred disruption vessel will be a sterile, 2 ml plastic microcentrifuge test tube capable of being used with the preferred BioSpec Products "Mini-Bead Beater" device, and the preferred beads will be 0.5 mm diameter zirconia silica beads from BioSpec Products. Other bead beating or cellular disruption systems may be used, so long as sufficient force can be applied for a period sufficient to mechanically disrupt the filtration medium and the fungal cells, whereby the size of the beads, the shape of the filter and the configuration of the disruption tube should permit maximal movement of the beads during the disruption process so that the cells and filtration medium receive as much force as possible from all directions.

Disruption is carried out by application of force to the vessel and for a time period sufficient that 1) the disrupting elements interact with the cells, tissue or spores such that the intracellular nucleic acid contents of the sample and/or micro-organisms in the sample are released into the liquid in the disruption chamber, and 2) the filtration medium is entirely disrupted such that no visible particles or fibers are apparent to the naked eye, but microscopic examination of the disrupted sample reveals the presence of individual microscopic filter particles, e.g., small glass fibers, suspended in the liquid.

Force can be imparted to the vessel by centrifugation, sonication, stirring, vortexing, mixing, shaking or other agitation, optionally in combination with chemical disruption (e.g. use of detergent).

Detection/Examination/Analysis

Following disruption of the sample, the disrupted mixture or a portion thereof, including nucleic acids as well as particles of the disrupted filtration medium, is recovered and subjected to further analysis, for example, melting curve analysis of PCR amplification products. Surprisingly, it has been found that suspended microscopic particles of the disrupted filtration medium do not interfere in any significant manner with the subsequent process of detection of the subcellular components, thereby eliminating the need for clearing of these particles prior to further analysis.

Detection of the nucleic acids of the disrupted mixture can be accomplished by any available method, including primer-directed amplification assay methods and nucleic acid hybridization methods. A variety of primer-directed nucleic acid amplification methods are known in the art including thermal cycling methods (e.g., PCR, RT-PCR, and LCR), isothermal methods, and strand displacement amplification (SDA). The preferred detection method is PCR. Following primer-directed amplification, amplification products can be analyzed using a variety of methods known in the art, including homogenous detection (e.g. melting curve analysis and 5' nuclease detection), standard non-denaturing gel electrophoresis (e.g., acrylamide or agarose) detection, denaturing gradient gel electrophoresis detection, and temperature gradient gel electrophoresis detection. The preferred method is melting curve analysis.

PCR-based detection, which is the preferred method of the present invention, comprises (a) performing PCR amplification of the sample using a suitable primer pair to produce a fungal nucleic acid PCR amplification result; and (b) examining the PCR amplification result of step (a) to detect for an amplification product of the primer pair, whereby a positive detection of the amplification product of the primer pair indicates the presence of target cells in the sample.

In carrying out the PCR, any suitable nucleic acid replication composition ("replication composition") in any format can be used. A typical replication composition for PCR amplification may comprise, for example, dATP, dCTP, dGTP, dTTP, target specific primers and a suitable polymerase. If the replication composition is in liquid form, suitable buffers known in the art may be used (Sambrook, J. et al. 1989, Molecular Cloning: A Laboratory Manual, Second Edition, Cold Spring Harbor Laboratory Press). Alternatively, if the replication composition is contained in a tablet form, then typical tabletization reagents may be included such as stabilizers and binding agents. Preferred tabletization technology is set forth in U.S. Pat. Nos. 4,762,857 and 4,678,812, each of which is hereby incorporated by reference in its entirety. A preferred replication composition of the instant invention comprises (a) at least one suitable primer pair for amplification of fungal nucleic acids; and (b) thermostable DNA polymerase.

Optionally, a replication composition may contain an internal positive control. The advantages of an internal positive control contained within a PCR reaction have been previously described in U.S. Pat. No. 6,312,930 and PCT Application No. WO 97/11197, each of which is hereby incorporated by reference in its entirety, and include: (i) the control may be amplified using a single primer; (ii) the amount of the control amplification product is independent of any target DNA or RNA contained in the sample; (iii) the control DNA can be tableted with other amplification reagents for ease of use and high degree of reproducibility in both manual and automated test procedures; (iv) the control can be used with homogeneous detection, i.e., without separation of product DNA from reactants; and (v) the internal control has a melting profile that is distinct from other potential amplification products in the reaction. Control DNA will be of appropriate size and base composition to permit amplification in a primer-directed amplification reaction. The control DNA sequence may be obtained from a fungal genome, or from another source, but must be reproducibly amplified under the same conditions that permit the amplification of the target amplification product. The control reaction is useful to validate the amplification reaction. Amplification of the control DNA occurs within the same reaction tube as the sample that is being tested, and therefore indicates a successful amplification reaction when samples are target negative, i.e. no target amplification product is produced. In order to achieve significant validation of the amplification reaction a suitable number of copies of the control DNA must be included in each amplification reaction.

In some instances it may be useful to include an additional negative control replication composition. The negative control replication composition will contain the same reagents as the replication composition but without the polymerase. The primary function of such a control is to monitor spurious background fluorescence in a homogeneous format when the method employs a fluorescent means of detection.

Replication compositions may be modified depending on whether they are designed to be used to amplify target DNA or the control DNA. Replication compositions that will amplify the target DNA (test replication compositions) may include (i) a polymerase (generally thermostable), (ii) a primer pair capable of hybridizing to the target DNA and (iii) necessary buffers for the amplification reaction to proceed. Replication compositions that will amplify the control DNA (positive control, or positive replication composition) may include (i) a polymerase (generally thermostable) (ii) the control DNA; (iii) at least one primer capable of hybridizing to the control DNA; and (iv) necessary buffers for the amplification reaction to proceed.

Homogenous detection refers to a preferred method for the detection of primer-directed amplification products where no separation (such as by gel electrophoresis) of amplification products from template or primers is necessary. Homogeneous detection is typically accomplished by measuring the level of fluorescence of the reaction mixture in the presence of a fluorescent dye. Homogenous detection includes "real-time" primer-directed nucleic acid amplifications (e.g., "real-time" PCR and "real-time" RT-PCR), methods for which are set forth in U.S. Pat. Nos. 6,171,785 and 5,994,056, each of which is hereby incorporated by reference in its entirety.

Melting curve analysis, one specific form of homogenous detection, detects and quantifies double stranded nucleic acid molecules ("dsDNA" or "target") by monitoring the fluorescence of the target amplification product ("target amplicon") during each amplification cycle at selected time points.

As is well known to the skilled artisan, the two strands of a dsDNA separate or "melt" when the temperature is higher than that dsDNA's melting temperature. Melting of a dsDNA molecule is a process, and under a given solution condition, melting starts at a temperature (designated $T_{MS}$ hereinafter), and completes at another temperature (designated $T_{ME}$ hereinafter). The familiar term, $T_m$, designates the temperature at which melting is 50% complete.

A typical PCR cycle involves a denaturing phase where the target dsDNA is melted, a primer annealing phase where the temperature is optimal for the primers to bind to the now-single-stranded target, and a chain elongation phase (at a temperature $T_E$) where the temperature is optimal for DNA polymerase to function.

According to the present invention, $T_{MS}$ should be higher than $T_E$, and $T_{ME}$ should be lower (often substantially lower) than the temperature at which the DNA polymerase is heat-inactivated. Melting characteristics are effected by the intrinsic properties of a given dsDNA molecule, such as the deoxynucleotide composition and the length of the dsDNA.

Intercalating dyes will bind to double stranded DNA. The dye/dsDNA complex will fluoresce when exposed to the appropriate excitation wavelength of light, which is dye dependent, and the intensity of the fluorescence may be proportionate to concentration of the dsDNA. Methods taking advantage of the use of DNA intercalating dyes to detect and quantify dsDNA are known in the art. Many dyes are known and used in the art for these purposes. The instant methods also take advantage of such relationship. Examples of such dyes include, but are not limited to, SYBR Green-I®, ethidium bromide, propidium iodide, TOTO®-1 {Quinolinium, 1-1'-[1,3-propanediylbis[(dimethyliminio)-3,1-propanediyl]]bis[4-[(3-methyl-2(3H)-benzothiazolylidene) methyl]]-, tetraiodide}, and YoPro® {Quinolinium, 4-[(3-methyl-2(3H)-benzoxazolylidene)methyl]-1-[3-(trimethylammonio)propyl]-,diiodide}. Most preferred for the instant invention is a non-asymmetrical cyanide dye such as SYBR Green-I®, manufactured by Molecular Probes, Inc. (Eugene, Oreg.).

Melting curve analysis is achieved by monitoring the change in fluorescence while the temperature is increased. When the temperature reaches the $T_{MS}$ specific for the target amplicon, the dsDNA begins to denature. When the dsDNA denatures, the intercalating dye dissociates from the DNA and fluorescence decreases. Mathematical analysis of the negative of the change of the log of fluorescence divided by the change in temperature plotted against the temperature results in the graphical peak known as a melting curve. The melting curve can in turn be used to determine the presence and quantity of target dsDNAs, from which the presence and level of target organisms can be determined. This method is very specific and sensitive. The fewest number of target dsDNA detectable is between one and 10 under typical reaction conditions and volumes.

In a preferred embodiment, PCR and DNA melting curve analysis is used to carry out homogenous detection, particularly with the BAX® System hardware and reagent tablets from Qualicon Inc (Wilmington, Del.). The details of the system are given in U.S. Pat. No. 6,312,930 and PCT Publication Nos. WO 97/11197 and WO 00/66777, each of which is hereby incorporated by reference in its entirety.

Another homogenous detection method is the 5' nuclease detection method, as set forth in U.S. Pat. Nos. 5,804,375, 5,538,848, 5,487,972, and 5,210,015, each of which is hereby incorporated by reference in its entirety.

A variety of other PCR detection methods are known in the art including standard non-denaturing gel electrophoresis (e.g., acrylamide or agarose), denaturing gradient gel electrophoresis, and temperature gradient gel electrophoresis. Standard non-denaturing gel electrophoresis is a simple and quick method of PCR detection, but may not be suitable for all applications.

Denaturing Gradient Gel Electrophoresis (DGGE) is a separation method that detects differences in the denaturing behavior of small DNA fragments (200-700 bp). The principle of the separation is based on both fragment length and nucleotide sequence. In fragments that are the same length, a difference as little as one base pair can be detected. This is in contrast to non-denaturing gel electrophoresis, where DNA fragments are separated only by size. This limitation of non-denaturing gel electrophoresis results because the difference in charge density between DNA molecules is near neutral and plays little role in their separation. As the size of the DNA fragment increases, its velocity through the gel decreases.

DGGE is primarily used to separate DNA fragments of the same size based on their denaturing profiles and sequence. Using DGGE, two strands of a DNA molecule separate, or melt, when heat or a chemical denaturant is applied. The denaturation of a DNA duplex is influenced by two factors: 1) the hydrogen bonds formed between complimentary base pairs (since GC rich regions melt at higher denaturing conditions than regions that are AT rich); and 2) the attraction between neighboring bases of the same strand, or "stacking". Consequently, a DNA molecule may have several melting domains with each of their individual characteristic denaturing conditions determined by their nucleotide sequence. DGGE exploits the fact that otherwise identical DNA molecules having the same length and DNA sequence, with the exception of only one nucleotide within a specific denaturing domain, will denature at different temperatures or Tm. Thus, when the double-stranded (ds) DNA fragment is electrophoresed through a gradient of increasing chemical denaturant, it begins to denature and undergoes both a conformational and mobility change. The dsDNA fragment will travel faster than a denatured single-stranded (ss) DNA fragment, since the branched structure of the single-stranded moiety of the molecule becomes entangled in the gel matrix. As the denaturing environment increases, the ds DNA fragment will completely dissociate and mobility of the molecule through the gel is retarded at the denaturant concentration at which the particular low denaturing domains of the DNA strand dissociate. In practice, the electrophoresis is conducted at a constant temperature (around 60° C.) and chemical denaturants are used at concentrations that will result in 100% of the DNA molecules being denatured (i.e., 40% formamide and 7M urea). This variable denaturing gradient is created using a gradient maker, such that the composition of each DGGE gel gradually changes from 0% denaturant up to 100% denaturant. Of course, gradients containing a reduced range of denaturant (e.g., 35% to 60%) may also be poured for increased separation of DNA.

The principle used in DGGE can also be applied to a second method that uses a temperature gradient instead of a chemical denaturant gradient. This method is known as Temperature Gradient Gel Electrophoresis (TGGE). This method makes use of a temperature gradient to induce the conformational change of dsDNA to ssDNA to separate fragments of equal size with different sequences. As in DGGE, DNA fragments with different nucleotide sequences will become immobile at different positions in the gel. Variations in primer design can be used to advantage in increasing the usefulness of DGGE for characterization and identification of the PCR products. These methods and principles of using primer design variations are described in PCR Technology Principles and Applications, Henry A. Erlich Ed., M. Stockton Press, NY, pages 71 to 88 (1988).

Packaging of Invention in Kit Format

In a further embodiment, the invention lends itself to a "kit" format, wherein the kit comprises a vessel which contains a predetermined amount of a selected enrichment/growth medium. The predetermined amount of a selected enrichment/growth medium is based on the particular type of sample to be enriched and the enrichment protocol associated therewith. Also included in the "kit" is a glass-fiber based filter that is easily amenable to disruption. In addition, the "kit" includes a vessel that further contains an effective amount of disruptive elements. The nature and quantity of disruptive elements should be effective to substantially disrupt the sample, or to substantially or entirely release the intracellular component being sought for further analysis, by application of the disruptive force to which the vessel is subjected. Optionally, the kit could further contain the reagents necessary to carry out the analysis of the nucleic acids, including the BAX® reagent tablet.

EXAMPLES

The invention is illustrated in the following examples. All parts, percentages, etc., referred to in the examples are by weight unless otherwise indicated.

Example 1

Evaluation of Filtration Media and Bead Milling Machines

A variety of filtration media such as membranes, and bench-top bead milling machines were assessed for the ability of the machine/membrane combination to disrupt the filtration media (membrane) sufficiently to allow for efficient breaking up of entrapped fungal cells using standard BAX System™ Yeast and Mold disruption tubes.

25 mm circles of the membrane filtration medium were placed in yeast and mold disruptor tubes (as described in Example 2) and bead-beaten for 15 min.

TABLE I

| Membrane Material | Source | Pore Size/ Retention | Bead Mill Disrupter Genie (Scientific Products) | Bead Mill Mini-Bead-Beater-1 ™ (BioSpec Products) | Bead Mill Mini-8 ™ (BioSpec Products) | Bead Mill Mini-96 ™ (BioSpec Products) |
|---|---|---|---|---|---|---|
| Tuffyn | Pall Corp. East Hills New York | 0.2 μm | Neg | Neg | Neg | Neg |
| Cellulose nitrate | Whatman | 0.45 μm | Neg | Neg | Neg | Neg |
| Polyethersulfone (Supor ®) | Pall Corp. | 0.2 μm | Neg | Neg | Neg | Neg |

TABLE I-continued

| Membrane Material | Source | Pore Size/ Retention | Bead Mill Disrupter Genie (Scientific Products) | Bead Mill Mini-Bead-Beater-1 ™ (BioSpec Products) | Bead Mill Mini-8 ™ (BioSpec Products) | Bead Mill Mini-96 ™ (BioSpec Products) |
|---|---|---|---|---|---|---|
| Polyethersulfone (Supor ®) | Pall Corp. | 0.45 µm | Neg | Neg | Neg | Neg |
| Glass Micro Fibre GF/A Whatman | Whatman | 1.6 µm (nominal) | Neg | Pos | Neg | Pos |

The designation "Neg" means that on gross examination, the filter was not disrupted by the process. The designation "Pos" means that on gross examination, the liquid in the tube appeared to be a milky liquid, and microscopic examination revealed small individual glass fibers in suspension. The only combinations that disrupted the membrane material were the Whatman GF/A filter with either the Mini-BeadBeater-1™ or Mini-BeadBeater-96™ from BioSpec Products.

Example 2

Detection and Measurement of Yeast Cell Concentration

The yeast *Saccharomyces cerevisiae* was used to artificially contaminate a flavored-water beverage at various levels of contamination. Following capture of these yeast on a filter, the presence of the yeast was detected through the utilization of melting curve analysis of resulting nucleic acid amplification product. Specifically, the BAX® System hardware and reagent tablets from Qualicon Inc. were used to perform this melting curve detection.

30 mL of beverage from each contamination level was filtered through a 25 mm-GF/A Glass Microfibre Filter with a 1.6 µm nominal pore size from (Whatman, Inc., Florham Park, N.J.). The filter was then placed in a 2-mL screw cap tube with:
(i) 1.0 mL of 0.4-0.6 mm Zirconia/Silica beads (ER120S obtained from
 Saint-Gobain Ceramics & Plastics, Northborough, Mass.);
(ii) 1 mL of Butterfields phosphate buffered saline; and
(iii) 0.05 mL of BAX™ DNA stabilizer reagent.

The tube was then processed for 5 min. in a Mini-Bead-Beater (BioSpec Products, Inc., Bartlesville, Okla.) disrupting both the yeast cells and the filter.

Subsequently, 600 µL of liquid was transferred to a new vessel and the DNA from the disrupted yeast cells was collected using an Invitrogen ChargeSwitch® serum kit (from Invitrogen Corporation, Carlsbad, Calif.) following the manufacturers protocol. The DNA was eluted into 100 µL BAX™ lysis buffer. 50 µL of the eluted DNA was used to hydrate a BAX System™ Yeast and Mold tablet. Amplification and analysis was then carried out on a BAX™ instrument.

TABLE II

| Sample No. | S. Cerevisiae No. of Cells per mL of Sample | BAX System ™ Yeast and Mold Detection Ratio |
|---|---|---|
| 1. | 33300 | 0.96 |
| 2. | 3330 | 0.90 |
| 3. | 330 | 0.63 |
| 4. | 33 | 0.10 |
| 5. | 0 | 0.00 (negative) |

These results demonstrate that the method of the present invention was able to successfully detect down to the lowest level of fungal cells utilized (33 cells/mL) without giving a false-positive result for the negative control (0 cells/mL) sample.

Example 3

PCR Analysis of Samples Prepared According to the Invention

In this experiment, examples of methods useful for testing with and without (i.e. direct testing) enrichment were determined. In the first step, the filterable liquid (sample) is filtered through a 25-mm GF/A Whatman Micro Fibre Filter. Disposable filter funnels can also be used. If interfering substances are suspected to be present, an additional volume of Butterfield's phosphate buffered saline or Peptone water can be run through the filter to wash out interfering material while retaining yeasts and molds.

In the second step, the filter is removed from the unit using clean (sterile for zero tolerance applications) forceps. The specific protocols for Direct Test and Enrichment Test are given below.

Direct Testing

Direct testing, i.e., without enrichment of the sample, is quantitative for over 1000 cells/mL of volume filtered. However, for a more sensitive direct assay, the BAX System™ DNA capture kit can be used. The contents are transferred to the Bead Only disruptor tube. 50 µL of DNA Stabilizer Plus is added to the tube. Then 1.2 mL of Butterfields Phosphate Buffer or Peptone water is added to the tube and the tube is capped. The tube is placed in a tube holder adaptor for Mini-Bead Beater-96™ and tightened in place. The bead-beating is carried out for 10 min., followed by spinning in a microcentrifuge for 1 min. 20 µL of bead-beaten sample is transferred to 200 µL Lysis reagent (lysis buffer with protease) followed by incubation for 20 min. at 37° C., and for 10 min. at 95° C. The sample is cooled on a chiller block for 5 min. 50 µL of the sample is added to a BAX System™ Yeast and Mold tablet on the chiller block. The tubes are capped followed by a run of Yeast and Mold direct cycle.

Testing after Enrichment

The filter is transferred to the BAX disruptor tube with enrichment media and incubated at 25° C. for 44 hours. 25 µA of DNA Stabilizer Plus is added to the tube. The tube is placed in a tube holder adaptor for Mini-Bead-Beater-96™ and tightened in place. The bead-beating is carried out for 10 min. followed by spinning in a microcentrifuge for 1 min. 20 µL of bead-beaten sample is transferred to 200 µL Lysis reagent (lysis buffer with protease) followed by incubation for 20 min. at 37° C., and for 10 min. at 95° C. The sample is cooled on a chiller block for 5 min. 50 µL of the sample is added to BAX System™ Yeast and Mold tablet on the chiller block. The tubes are capped followed by a run of Yeast and Mold direct cycle.

Example 4

Detection of Yeast in Liquid Samples Using Different Types of Filters

In this experiment, the yeast *Saccharomyces cerevisiae* was used to artificially contaminate a flavored-water beverage at various levels of contamination. Four levels of contamination were used, as well as a negative control containing no spiked yeast cells. Duplicate 5 mL aliquots of each of these contaminated samples were then filtered through a Whatman GF/A glass microfiber filter, shown in Table I above to be disrupted under the method of the present invention, or a Pall Supor filter, shown in Table I to not be properly disrupted under the method of the present invention. Filters were then transferred to BAX® Yeast and Mold Disruptor Tubes and processed according to the disruption protocol outlined in the Direct Testing method of Example 3, above. The amount of DNA liberated from the filter/sample and presence/absence of yeast in each sample was detected through the utilization of melting curve analysis of nucleic acid amplification products, also as described in Example 3, above.

| No. of S. Cerevisiae | BAX Ratio Relative Quantity of DNA Liberated from Filter | | | | BAX System ™ Machine Generated Positive/Negative Sample Determination | | | |
|---|---|---|---|---|---|---|---|---|
| Cells Per 5 mL of Sample | Whatman Filter Rep. 1 | Whatman Filter Rep. 2 | Supor Filter Rep. 1 | Supor Filter Rep. 2 | Whatman Filter Rep. 1 | Whatman Filter Rep. 2 | Supor Filter Rep. 1 | Supor Filter Rep. 2 |
| 200,000 | 0.94 | 0.85 | 0.71 | 0.66 | Pos. | Pos. | Pos. | Pos. |
| 20,000 | 0.83 | 0.84 | 0.27 | 0.15 | Pos. | Pos. | Pos. | Pos. |
| 2,000 | 0.46 | 0.24 | 0 | 0 | Pos. | Pos. | Neg. | Neg. |
| 200 | 0.09 | 0.04 | 0 | 0 | Pos. | Neg. | Neg. | Neg. |
| 0 | 0 | 0 | 0 | 0 | Neg. | Neg. | Neg. | Neg. |

The results demonstrate that the Supor filter media, which remains intact during disruption, interferes with efficient release of DNA from the yeast cells during the disruption process. This, in turn, causes lower sensitivity in detection of organisms in the starting sample, as evidenced by the negative results obtained when 2,000 cells or fewer were present on the filter. In contrast, the Whatman glass microfiber filter is completely destroyed during the disruption process, allowing for more efficient DNA release from cells and, consequently, more sensitive detection of contaminating cells in a sample, with these filters allowing detection of 2,000 or even 200 cells on the filter. The detection sensitivity is therefore increased by 1-2 orders of magnitude by use of the glass microfiber filter.

Example 5

Yeast Detection in Filterable Liquids

In this experiment, the analytical procedure of the present invention was compared with the reference procedure. In the present invention, the yeast and mold samples (i.e., filterable liquids) were BAX™-enriched for 44 hours. The reference procedure follows a 5-day enrichment period.

Eight bottles of Dasani™ brand uncarbonated raspberry-flavored water were spiked with the yeast *Saccharomyces cerevisiae* at a target level of 5 colony forming units (CFU)/bottle. The bottles were labeled 1-8. Two bottles were left unspiked. They were labeled U1 and U2.

Reference Procedure

The entire contents of bottles 1-4 (spiked) and one unspiked bottle (Y1) were each filtered through a 0.45-µm pore size, 47-mm diameter nitrocellulose membrane.

After filtration, the filters were placed on Dichloran Rose Bengal Chloramphenicol (DRBC) Agar plates and incubated at 25° C., for 5 days. After 5 day the colonies were counted.

Invention Procedure

The entire contents of bottles 5-8 and one unspiked bottle (Y2) were each filtered through sterile 25-mm Whatman GF/A filters (catalog #1820-025; 25-mm glass microfibre filter).

Following filtration, the filters were placed in BAX® System Yeast and Mold disrupter tubes. The tubes contained growth media and disruption beads. The filters were incubated for 44 hours, at 25° C. Subsequently, 50 µl of BAX System™ DNA Stabilizer Reagent was added to each tube before bead-beating for 10 min. on a BioSpec Mini-Bead-Beater 96™.

Following the step of bead-beating, the material was analyzed for the presence of fungal (yeast and mold) DNA using the BAX System™ Yeast and Mold kit as described by the manufacturer.

The results of the analysis using the reference procedure and the invention procedure are provided in Table IV.

TABLE IV

| Bottle No. | Target Spike Level | Reference Filtration Plating (5 days to result) | BAX ™ Yeast Mold Filtered Liquid Protocol (44 hours to result) |
|---|---|---|---|
| 1 | 5 CFU | 5 | Not Performed |
| 2 | 5 CFU | 2 | Not Performed |
| 3 | 5 CFU | 5 | Not Performed |
| 4 | 5 CFU | 5 | Not Performed |
| Y1 | 0 | 0 | Not Performed |
| 6 | 5 CFU | Not Performed | Positive |
| 7 | 5 CFU | Not Performed | Positive |
| 8 | 5 CFU | Not Performed | Positive |
| 9 | 5 CFU | Not Performed | Positive |
| Y2 | 0 | Not Performed | Negative |

All of the spiked 44-hour enriched samples (Bottles 6-9) were positive and the unspiked (blanks; Y1 and Y2) negative. The BAX System™ Yeast and Mold assay can detect low levels of fungi in large volumes of filterable liquid after 44-hour enrichment. This result is comparable to that received utilizing the reference procedure.

Example 6

Mold Detection in Filterable Liquids

In this experiment, the analytical procedure of the present invention was compared with the reference procedure. In the present invention, the yeast and mold samples (i.e., filterable liquids) were BAX®-enriched for 44 hours. The reference procedure follows a 5-day enrichment period.

Twenty bottles of a filterable bottled beverage were spiked with the mold *Aspergillus niger* at a target level of 5 CFU/bottle. The bottles were labeled 1-20. Two bottles were left unspiked. They were labeled M1 and M2.

Reference Procedure

The entire contents of bottles 1-10 (spiked) and one unspiked bottle (M1) were each filtered through a 0.45-µm pore size, 47-mm diameter nitrocellulose membrane.

After filtration, the filters were placed on Dichloran Rose Bengal Chloramphenicol (DRBC) Agar plates and incubated at 25° C., for 5 days. After 5 day the colonies were counted.

Invention Procedure

The entire contents of bottles 11-20 and one unspiked bottle (M2) were each filtered through sterile 25-mm Whatman GF/A filters (catalog #1820-025; 25-mm glass microfibre filter).

Following the filtration step, the filters were placed in BAX System® Yeast and Mold disrupter tubes. The tubes contained growth media and disruption beads. The filters were incubated for 44 hours, at 25° C. Subsequently, 50 µl of BAX System™ DNA Stabilizer Reagent was added to each tube before bead-beating for 10 min. on a BioSpec Mini-Bead-Beater 96™.

Following the step of bead-beating, the material was analyzed for the presence of fungal (yeast and mold) DNA using the BAX System™ Yeast and Mold kit as described by the manufacturer.

The results of the analysis using the reference procedure and the invention procedure are provided in Table V.

TABLE V

| Bottle No. | Target Spike Level | Reference *A. Niger* Actual CFU/Plate | BAX ™ Yeast and Mold Filtered Liquid Protocol (44 hours to result) |
|---|---|---|---|
| 1 | 5 CFU | 4 | Not Performed |
| 2 | 5 CFU | 5 | Not Performed |
| 3 | 5 CFU | 8 | Not Performed |
| 4 | 5 CFU | 6 | Not Performed |
| 5 | 5 CFU | 5 | Not Performed |
| 6 | 5 CFU | 4 | Not Performed |
| 7 | 5 CFU | 8 | Not Performed |
| 8 | 5 CFU | 10 | Not Performed |
| 9 | 5 CFU | 6 | Not Performed |
| 10 | 5 CFU | 6 | Not Performed |
| M1 | 0 | 0 | Not Performed |
| 12 | 5 CFU | Not Performed | Positive |
| 13 | 5 CFU | Not Performed | Positive |
| 14 | 5 CFU | Not Performed | Positive |
| 15 | 5 CFU | Not Performed | Positive |
| 16 | 5 CFU | Not Performed | Positive |
| 17 | 5 CFU | Not Performed | Positive |
| 18 | 5 CFU | Not Performed | Positive |
| 19 | 5 CFU | Not Performed | Positive |
| 20 | 5 CFU | Not Performed | Positive |
| 21 | 5 CFU | Not Performed | Positive |
| M2 | 0 | Not Performed | Negative |

The actual CFU/bottle numbers ranged from 4-10, based on traditional plating results. All spiked bottles tested by the new system were positive. The BAX System™ Yeast and Mold kit successfully detected the presence of small numbers of fungal spores in a filterable liquid without returning a false-positive result on the negative (unspiked) sample. This result is comparable to that received utilizing the reference procedure.

What is claimed is:

1. A process for preparing a sample comprising fungal cells for analytical testing of the nucleic acids of said fungal cells, comprising the steps of:
   (i) preparing said sample in the form of a filterable liquid;
   (ii) filtering said filterable liquid using a glass microfiber filter wherein said fungal cells from said sample form a retentate on said glass microfiber filter;
   (iii) transferring said glass microfiber filter to a vessel suitable for disrupting said glass microfiber filter and said fungal cells by mechanical means;
   (iv) simultaneously disrupting said fungal cells and said glass microfiber filter using mechanical means with a force sufficient to disrupt said glass microfiber filter into microscopic particles;
   wherein said microscopic particles of said disrupted glass microfiber filter are not removed from the nucleic acids of said fungal cells of said sample prior to analytical testing; and
   (v) analytically testing the disrupted fungal cells and glass microfiber filter of step (iv) using amplification and melting curve analysis of PCR amplification product derived from the nucleic acids of the sample.

2. The process as recited in claim 1, wherein said fungal cells are yeast or mold cells.

3. The process as recited in claim 1, wherein said sample is a food or beverage sample.

4. The process as recited in claim 1, wherein said glass microfiber filter has a 1.6 µm nominal pore size.

5. The process as recited in claim 1, wherein said vessel is a test tube or a microcentrifuge tube.

6. The process as recited in claim 1, wherein said mechanical means in step (iv) is bead beating.

7. The process as recited in claim 1 further comprising the step of enrichment of said sample for growth of said fungal cells, wherein said enrichment is carried out either a) prior to said filtering of said filterable liquid in step (ii) of claim 1; b) subsequent to said filtering of said filterable liquid in step (ii) of claim 1 but prior to said disrupting of said fungal cells in step (iv) of claim 1; or c) both prior to said filtering of said filterable liquid in step (ii) of claim 1 and subsequent to said filtering of said filterable liquid in step (ii) of claim 1 but prior to said disrupting of said fungal cells and said glass microfiber filter in step (iv) of claim 1.

8. The process as recited in claim 1, wherein said simultaneous disrupting is accomplished by:
   (i) providing beating beads and liquid into said disruption vessel; and
   (ii) subjecting the contents of said disruption vessel to the force of a bead-mill for a period of time sufficient to disrupt said filter into suspended fibers.

9. The process as recited in claim 1, wherein said filtering comprises vacuum filtration.

10. A process for preparing a food or beverage sample comprising fungal cells for melting curve analysis of PCR amplification products produced from the nucleic acids of said fungal cells, comprising the steps of:
   a. preparing said sample in the form of a filterable liquid;
   b. filtering said filterable liquid using vacuum filtration through a glass microfiber filter wherein said fungal cells from said sample form a retentate on said filter;

c. transferring said filter to a vessel suitable for disrupting said filter and said fungal cells using bead beating;

d. simultaneously disrupting said fungal cells and said filter by bead beating said vessel using a bead beater for a time period and a force sufficient to disrupt said filter into individual suspended glass fibers;

wherein said suspended glass fibers are not removed from the nucleic acid contents of said fungal cells of said sample prior to direct PCR analysis; and e. analytically testing the disrupted fungal cells and glass microfiber filter of step d. using amplification and melting curve analysis of PCR amplification product derived from the nucleic acids of the sample.

11. The process as recited in claim 10 further comprising the step of enrichment of said sample for growth of said fungal cells, wherein said enrichment is carried out either a) prior to said filtering of said filterable liquid in step b of claim 10; b) subsequent to said filtering of said filterable liquid in step b of claim 10 but prior to said disrupting of said fungal cells in step d of claim 10; or c) both prior to said filtering of said filterable liquid in step b of claim 10 and subsequent to said filtering of said filterable liquid in step b of claim 10 but prior to said disrupting of said fungal cells and said filter in step d of claim 10.

* * * * *